United States Patent [19]

Bourdoulous et al.

[11] Patent Number: 5,464,157

[45] Date of Patent: Nov. 7, 1995

[54] NEBULIZER FOR USE IN AN ATOMIC ABSORPTION SYSTEM

[75] Inventors: Robert P. Bourdoulous, Shelton; John Vollmer, Newtown, both of Conn.

[73] Assignee: The Perkin-Elmer Corporation, Norwalk, Conn.

[21] Appl. No.: 276,144

[22] Filed: Jul. 18, 1994

[51] Int. Cl.$^6$ .................................................. B05B 9/03
[52] U.S. Cl. ................. 239/424; 239/433; 239/DIG. 19; 356/315
[58] Field of Search .................................. 239/337, 338, 239/340, 346, 418, 423, 424, 424.5, 429, 433, 434.5, DIG. 19; 356/315, 346

[56] References Cited

U.S. PATENT DOCUMENTS

| | | | |
|---|---|---|---|
| 2,847,899 | 8/1958 | Walsh | 356/315 |
| 3,177,758 | 4/1965 | Isreeli | 356/315 X |
| 3,430,864 | 3/1969 | Miller et al. | 356/315 X |
| 3,550,858 | 12/1970 | Herron et al. | 239/338 |
| 4,125,225 | 11/1978 | Venghiattis | 239/338 |
| 4,220,413 | 9/1980 | Targowski et al. | 356/315 |
| 4,330,490 | 5/1982 | Higgins | 239/338 X |
| 4,865,444 | 9/1989 | Green et al. | 356/315 X |
| 4,886,359 | 12/1989 | Berndt | 356/315 X |
| 5,186,621 | 2/1993 | Pennington | 356/315 X |

Primary Examiner—Andres Kashnikow
Assistant Examiner—Lesley D. Morris
Attorney, Agent, or Firm—Edwin T. Grimes

[57] ABSTRACT

The present invention is directed to a nebulizer for use in an atomic absorption system which includes a capillary assembly having a capillary holder having an internal axial passage therethrough, a sapphire capillary tip mounted on one end of the capillary holder and the other end of the holder being connected to a sample liquid source through a capillary gland nut assembly. A venturi member is provided which has an inlet portion, a throat portion and an exiting bell shaped portion. A body assembly has one end connected to the venturi member. The capillary assembly is mounted on the body assembly for axial movement so that the capillary holder partially enters the venturi inlet portion and the capillary tip enters the venturi throat. Compressed oxidant is supplied to the venturi member in the vicinity of the capillary tip so as to suck sample liquid from the capillary tip to form a mixture of fine liquid mist and gas which is discharged through the exiting bell shaped portion.

8 Claims, 2 Drawing Sheets

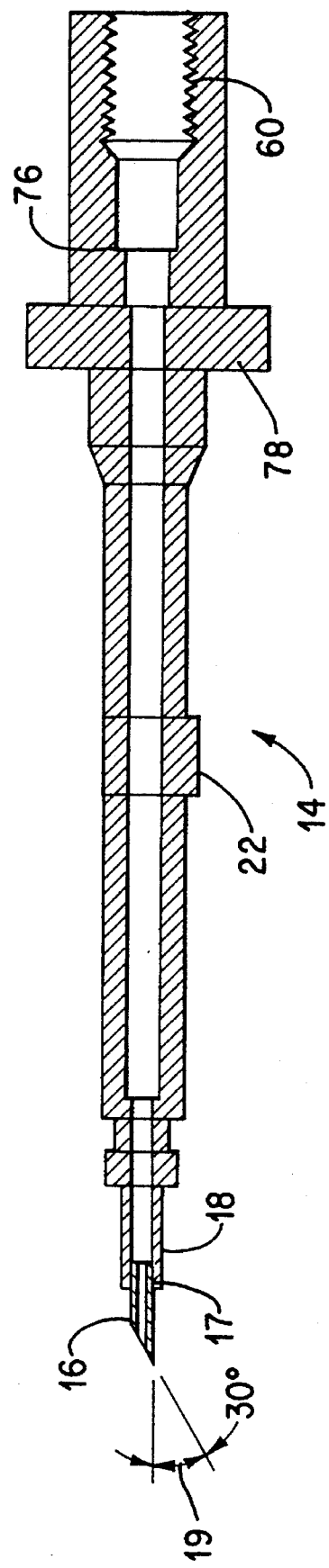
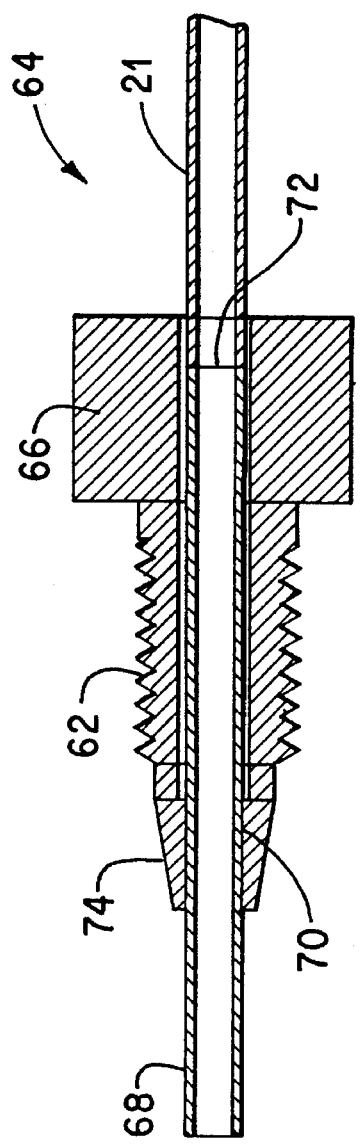
FIG. 2
FIG. 3

NEBULIZER FOR USE IN AN ATOMIC ABSORPTION SYSTEM

FIELD OF INVENTION

This invention relates generally to atomic absorption spectroscopy and more particularly to nebulizers associated therewith.

BACKGROUND OF THE INVENTION

In atomic absorption spectroscopy, the measurement of the absorption of a radiation beam at a characteristic resonant spectral line for a particular element yields a measure of the concentration of that element in an original sample solution. One of the most common techniques for atomizing an element for purposes of the absorption measurement is by introducing a liquid sample solution of the element of interest into a gas burner wherein droplets of the solution are vaporized and the element ultimately atomized, so as to form in the path of the apparatus radiation beam, a substantial quantity of the element of interest in its atomic state.

In order to effect appropriate burning of the element containing solution, the liquid must be converted into a fine spray and then mixed with a fuel and oxidant gas before introduction into the burner. The fine spray is achieved through the use of a nebulizer, such as described in U.S. Pat. No. 4,125,225, also assigned to the assignee herein.

A nebulizer, generally, employs a venturi-type restriction which passes rapidly moving gas (hereinafter referred to as an oxidant) past an opening, drawing a portion of the liquid sample solution into the gas stream, effecting an atomizing of the liquid in the process. The liquid is said to be aspirated by the venturi effect caused by the rapidly moving current of gas.

The sample laden gas or oxidant, then passes into the burner chamber where it is mixed with additional oxidant from an auxiliary inlet, and fuel such as acetylene. It is then introduced into the burner head where it is ignited.

The nebulizer of Pat. No. 4,125,225 is characterized by a capillary tubing which is a continuous corrosion-resistant single tube that extends all the way from its aspirated tip at one end to the liquid sample supply at the other end thereof. The present invention is directed to improvements over this prior art nebulizer, as will become clear as the description proceeds.

SUMMARY OF THE INVENTION

The present invention is directed to a new and improved nebulizer for use in an atomic absorption system which includes, in combination, a capillary assembly which includes a capillary holder having an internal axial passage therethrough, and a sapphire capillary tip mounted on one end. In one form of the invention a capillary gland nut assembly is threadably mounted on the other end of the capillary holder. This assembly includes a capillary gland nut, a teflon tube fixedly connected to the gland nut by a press fit, a sample supply tube having one end inserted in the gland nut to abut one end of the teflon tube in fluid flow communication. The other end of the sample supply tube is connected to a source of sample liquid. The gland nut engages the capillary holder to form a seal therebetween. The other end of the teflon tube is in fluid flow communication with the axial passage. The nebulizer further includes a venturi member having an inlet portion, a throat portion and an exiting bell shaped portion. In addition, in one form of the invention, the nebulizer includes a body assembly having one end connected to the venturi member. Means are provided for mounting the capillary assembly in the body assembly for axial movement so that the capillary holder partially enters the venturi inlet portion and the capillary tip enters the venturi throat. Means are provided for supplying compressed oxidant to the venturi member in the vicinity of the capillary tip so as to suck sample liquid from the capillary tip to form a mixture of fine liquid mist and gas which is discharged through the exiting bell shaped portion of the venturi member.

According to one aspect of the invention the holder is fabricated from poly ether ether ketone and has a length of the order of about 6.35 millimeters. The capillary tip has an outside diameter of about 0.76 millimeters and extends outwardly from the end of said capillary holder about 3.05 millimeters According to another aspect of the invention the venturi throat portion of the venturi member has a diameter of the order of about 0.92 millimeters and the exiting bell shaped portion is parabolic and is defined by the interface of a radius of about 7.16 millimeters and an included taper of about 10°.

Other objects and advantages will become apparent to those skilled in the art from the following detailed description read in conjunction with the appended claims and drawings attached hereto.

BRIEF DESCRIPTION OF THE DRAWINGS

FIG. 2 is a cross-sectional view along the center-line of a capillary tube holder of FIG. 1; and FIG. 3 is a cross-sectional view along the center-line of a capillary gland nut assembly of FIG. 1.

DESCRIPTION OF PREFERRED EMBODIMENTS

Figure 1:
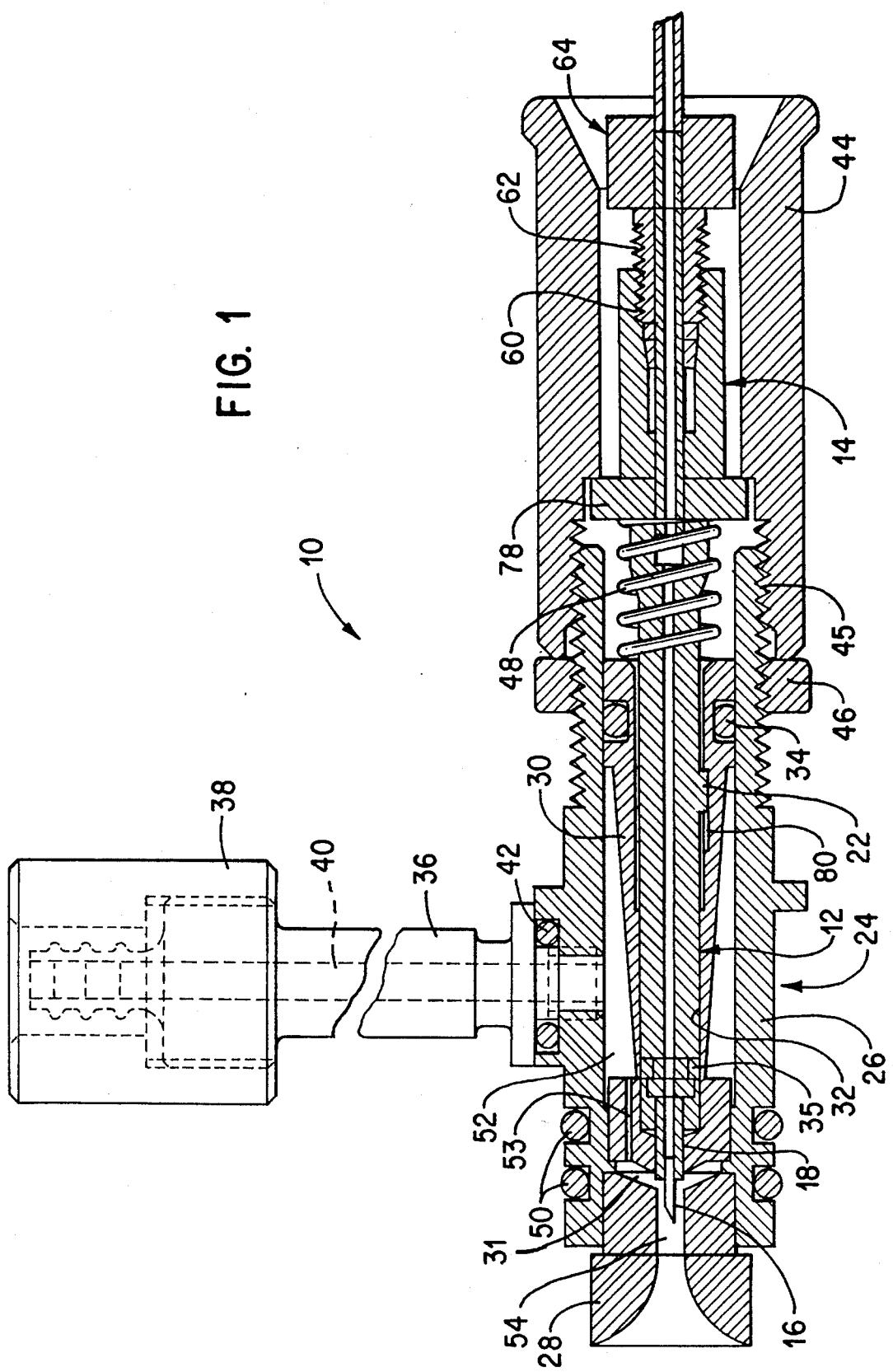
FIG. 1 is a cross-sectional view along the center-line of a nebulizer constructed according to the concepts of the invention.

Referring to FIG. 1, a nebulizer 10 for use in an atomic absorption system includes a capillary assembly, indicated at This assembly comprises a capillary tube holder 14 which has at one end thereof a small inside diameter to accept a sapphire capillary tip 16. The tip is fixedly connected to the holder 14 by a press fit, as indicated at 17, FIG. 2, to provide a sealed connection therebetween. The tip 16 has an inside diameter of about 0.398 millimeters and an outside diameter of about 0.76 millimeters This tip is constructed and arranged to enter a venturi throat 54, FIG. 1, of a venturi member 28. The capillary tube holder 14 has an outside diameter portion, indicated at 18, of about 1.55 millimeters, which gives it strength but allows it to partially enter the venturi inlet portion 31. The capillary tip 16 is fabricated from sapphire which is corrosion resistant to most materials and hence is serviceable for substantially all chemical solutions for atomic absorption sampling. The sapphire tip is about 4.06 millimeters long and extends outwardly from the end of the holder 14 about 3.05 millimeters The tip 16 has an angular cut at the end thereof of about 30° on the protruding end. The capillary tube holder 14 is fabricated from poly ether ether ketone (PEEK).

The capillary tube holder 14 has at the other end thereof an internally threaded portion 60 which engages an externally threaded portion 62 of a capillary gland nut assembly 64, FIG. 3. The capillary gland nut assembly includes a capillary gland nut 66 and a teflon tube 68 which is fixedly connected to the gland nut 66 by a press fit, as indicated at 70, FIG. 3, to provide a sealed connection therebetween. The capillary gland nut 66 is fabricated from polypropylene (natural). The gland nut assembly 64 also includes sample supply tubing 21 of polyethylene, which extends to the source of the sample liquid. This tubing is inserted into the end of the gland nut 66 until it abuts the teflon tube The gland nut 66 has a tapered surface, indicated at 74. In operation the capillary gland nut assembly 64 is threadably inserted into the capillary tube holder 14 until the tapered surface 74 engages a shoulder 76 on the holder 14. This ensures a seal between the capillary gland nut assembly 64 and the capillary tube holder 14.

The nebulizer 10 further includes a body assembly indicated generally at 24, which includes a main body portion 26 that is machined on one end to press fit a venturi member 28. The main body portion is machined on the other end to press fit a spool shaped piece 30 that guides the capillary assembly. The venturi member 28 is fabricated from poly ether ether ketone (PEEK) and has a throat 54 diameter of about a 0.92 millimeters and an exiting smooth bell shaped portion 56 which is parabolic and is defined by the interface of a radius of about 7.16 millimeters and an inclined taper angle of about 10°. The venturi has an inlet portion as indicated at 31. The inside surface of the spool piece 30 on one end thereof, as indicated at 32, serves to guide the capillary assembly 12. A spool O-ring 34 seals the outside surface of the spool piece 30 to the inside surface of the body portion 26. An O-ring 35 seals the outside surface of the capillary holder 14 with respect to the inside surface of the spool piece 30.

The capillary holder 14 is provided with a protruding key portion 22 which slides in a mating longitudinal slot 80 in the spool piece 30. This key acts as a guide so the capillary does not rotate during adjustment, and stays in its optimum location. This optimum location is where the 30° angle "faces up" or is 30° from the horizontal, as indicated at 19, FIG. 2.

A nebulizer body extension member 36, FIG. 1, serves to transport oxidant to the nebulizer body assembly 24. A nut connector 38 compresses an oxidant supply line tube 40 to the extension 36, insuring a proper seal. An O-ring 42 is provided to seal one end of the extension member 36 to the nebulizer body portion 26.

A capillary adjustment nut 44 is threadably mounted on said main body portion 26 as at 45. This adjustment nut serves to move the capillary tip 26 axially into the throat of the venturi member 28 to position same for operation. A capillary lock nut 46 is also threadably mounted on the main body portion 26 to lock or retain the capillary adjustment nut 44 in its set position. A compression spring 48 acts between a shoulder 78 on capillary tube holder 14 and the spool piece 30 to keep the capillary assembly always biased in one axial direction. A pair of O-rings 50 seals the nebulizer body assembly 24 inside an end cap (not shown).

In operation, compressed gas enters through oxidant supply line tube 40 and proceeds through an annular passage 52 and axial bores 53 in the spool piece part 30 into the restricted throat 54 of the venturi member 28. The gas in the throat is moving at quite high speed and at relatively low absolute pressure, approximately 11 in. Hg. vacuum, so as to suck the liquid sample at the sapphire capillary tip 16 along with the rapidly moving gas. At the same time the liquid is broken up into extremely small droplets thereby forming a mixture of gas and a fine liquid spray or mist, which spreads or diffuses in the expansion or bell shaped portion 56 of the venturi member. This mixture is fed to a burner chamber of an atomic absorption system.

It will thus be seen that the present invention does indeed provide a new and improved nebulizer wherein all sample wetted surfaces are polymer, or sapphire or other non-metal corrosion resistant material, whereby one nebulizer can service substantially all chemical solutions for atomic absorption sampling.

Although certain particular embodiments of the invention are herein disclosed for purposes of explanation, further modifications thereof, after study of the specification, will be apparent to those skilled in the art to which the invention pertains. Reference should accordingly be had to the appended claims in determining the scope of the invention.

We claim:

1. A nebulizer for use in an atomic absorption system comprising, in combination:

a) a capillary assembly including
   i) a capillary holder,
   ii) a sapphire capillary tip mounted on one end of said capillary holder and the end of said holder being connected to a sample liquid source; said capillary tip having an outside diameter of about 0.76 millimeters b) a venturi member having an inlet portion, a throat portion and an exiting bell shaped portion; said throat portion having an inside diameter of about 0.92 millimeters;

c) a body assembly having one end connected to said venturi member;

d) means mounting said capillary assembly in said body assembly for axial movement so that said capillary holder partially enters said venturi inlet portion and said capillary tip enters said venturi throat portion; and e) means for supplying compressed oxidant to said venturi member in the vicinity of said capillary tip so as to suck sample liquid from said capillary tip to form a mixture of fine liquid mist and gas which is discharged through said exiting bell shaped portion of the venturi member.

2. A nebulizer according to claim 1 wherein said capillary holder is fabricated from polyether ether ketone and has a length of the order of about 6.35 millimeters and said capillary tip extends outwardly from the end of said capillary holder about 3.05 millimeters 3. A nebulizer according to claim 1 wherein said exiting bell shaped portion of said venturi member is parabolic and is defined by the interface of a radius of about 7.16 millimeters and an included taper angle of about 10°.

4. A nebulizer according to claim 1 wherein said sapphire capillary tip has an angular cut at a protruding end thereof of about 30° with respect to the horizontal, whereby said angle faces up.

5. A nebulizer for use in an atomic absorption system comprising, in combination:

a) a capillary assembly including
   i) a capillary holder having an internal axial passage therethrough,
   ii) a sapphire capillary tip mounted on one end of the capillary holder in fluid flow communication with said axial passage,
   iii) a capillary gland nut assembly threadably mounted on another end of said capillary holder, said capillary gland nut assembly including a capillary gland nut, a teflon tube fixedly connected to the gland nut by a press fit, a sample supply tube having one end inserted in said gland nut to abut one end of said teflon tube in fluid flow communication, another end of said sample supply tube being connected to a source of sample liquid, said gland nut engaging said capillary holder to form a seal therebetween, another end of said teflon tube being in fluid flow communication with said axial passage;

b) a venturi member having an inlet portion, a throat portion and an exiting bell shaped portion;

c) a body assembly having one end connected to said venturi member;

d) means mounting said capillary assembly in said body assembly for axial movement so that said capillary holder partially enters said venturi inlet portion and said capillary tip enters said venturi throat portion; and e) means for supplying compressed oxidant to said venturi member in the vicinity of said capillary tip so as to suck sample liquid from said capillary tip to form a mixture of fine liquid mist and gas which is discharged through said exiting bell shaped portion of the venturi member.

6. A nebulizer for use in an atomic absorption system comprising, in combination:

a) a capillary assembly including
  i) a capillary holder having an internal axial passage therethrough,
  ii) a sapphire capillary tip mounted on one end of the capillary holder in fluid flow communication with said axial passage,
  iii) a capillary gland nut assembly threadably mounted on another end of said capillary holder, said capillary gland nut assembly including a capillary gland nut, a teflon tube fixedly connected to the gland nut by a press fit, a sample supply tube having one end inserted in said gland nut to abut one end of said teflon tube in fluid flow communication, another end of said sample supply tube being connected to a source of sample liquid, said gland nut engaging said capillary holder to form a seal therebetween, another end of said teflon tube being in fluid flow communication with said axial passage;

b) a venturi member having an inlet portion, a throat portion and an exiting bell shaped portion;

c) a body assembly including
  i) a main body portion having one end connected to said venturi member,
  ii) a spool shaped part connected to another end of said main body portion, said spool part having an inside surface shaped for guiding said capillary assembly,
  iii) a means for sealing an outside surface of the spool part with respect to said body portion,
  iv) means for sealing an outside surface of said capillary holder with respect to said spool part;

d) a capillary adjustment nut threadably mounted on said main body portion to move said capillary assembly axially with respect to said main body portion so that said capillary holder partially enters said venturi inlet portion and said capillary tip enters said venturi throat portion, means for preventing the capillary assembly from rotating during axial adjustment;

e) a capillary lock nut threadably mounted on said main body portion to lock said adjustment nut in a selected position;

f) a nebulizer body extension assembly connected to said body assembly to transport compressed oxidant to said venturi member in the vicinity of said capillary tip so as to suck sample liquid from said capillary tip to form a mixture of fine liquid mist and gas which is discharged through said exiting bell shaped portion of the venturi member.

7. A nebulizer for use in an atomic absorption system comprising, in combination:

a) a capillary assembly including
  i) a capillary holder having an internal axial passage therethrough,
  ii) a sapphire capillary tip mounted on one end of the capillary holder in fluid flow communication with said axial passage,
  iii) a capillary gland nut assembly threadably mounted on another of said capillary holder, said capillary gland nut assembly including a capillary gland nut, a teflon tube fixedly connected to the gland nut by a press fit, a sample supply tube having one end inserted in said gland nut to abut one end of said teflon tube in fluid flow communication, another of said sample supply tube being connected to a source of sample liquid, said gland nut having a tapered surface which engages a shoulder on said capillary holder to form a seal therebetween, another of said teflon tube being in fluid flow communication with said axial passage;

b) a venturi member having an inlet portion, a throat portion and an exiting bell shaped portion;

c) a body assembly including
  i) a main body portion having one end connected to said venturi member,
  ii) a spool shaped part connected to another end of said main body portion, said spool part having an inside surface constructed and arranged for guiding said capillary assembly,
  iii) a spool O-ring for sealing an outside surface of the spool part with respect to an inside surface of said body portion,
  iv) a second O-ring for sealing an outside surface of said capillary holder with respect to an inside surface of said spool part;

d) a capillary adjustment nut threadably mounted on said main body portion to move said capillary assembly axially with respect to said main body portion so that said capillary holder partially enters said venturi inlet portion and said capillary tip enters said venturi throat portion, means for preventing the capillary assembly from rotating during axial adjustment;

e) a capillary lock nut threadably mounted on said main body portion to lock said adjustment nut in a selected position;

f) a compression spring mounted between said capillary holder and said spool shaped part to bias said capillary assembly in one axial direction; and g) a nebulizer body extension assembly connected to said body assembly to transport compressed oxidant to said venturi member in the vicinity of said capillary tip so as to suck sample liquid from said capillary tip to form a mixture of fine liquid mist and gas which is discharged through said exiting bell shaped portion of the venturi member.

8. A nebulizer according to claim 6 further comprising a compression spring mounted between said capillary holder and said spool shaped part to bias said capillary in an axial direction.

* * * * *

UNITED STATES PATENT AND TRADEMARK OFFICE
CERTIFICATE OF CORRECTION

PATENT NO. : 5,464,157
DATED : November 7, 1995
INVENTOR(S) : Robert P. Bourdoulous et al.

It is certified that error appears in the above-indentified patent and that said Letters Patent is hereby corrected as shown below:

Column 2, line 44, after "at" insert --12.--

Column 3, line 9, after "tube" insert --68 as at 72.--

Column 3, line 50, delete "26" and insert --16--

Column 3, line 61, delete "part"

Column 4, line 23, delete "the" and insert --another--

Column 4, line 46, after "the" insert --one--

Column 6, line 15, after "another" insert --end--

Column 6, line 19, after "another" insert --end--

Column 6, line 23, after "another" insert --end--

Signed and Sealed this

Thirteenth Day of February, 1996

Attest:

BRUCE LEHMAN

*Attesting Officer*     *Commissioner of Patents and Trademarks*